(12) United States Patent
Kimura

(10) Patent No.: US 7,756,562 B2
(45) Date of Patent: Jul. 13, 2010

(54) APPARATUS AND METHOD FOR ANALYZING BLOOD FLOW

(75) Inventor: Tokunori Kimura, Yaita (JP)

(73) Assignees: Kabushiki Kaisha Toshiba, Minato-Ku, Tokyo (JP); Toshiba Medical Systems Corporation, Otawara-Shi, Tochigi-Ken (JP)

( * ) Notice: Subject to any disclaimer, the term of this patent is extended or adjusted under 35 U.S.C. 154(b) by 1439 days.

(21) Appl. No.: 10/946,104

(22) Filed: Sep. 22, 2004

(65) Prior Publication Data

US 2005/0065432 A1  Mar. 24, 2005

(30) Foreign Application Priority Data

Sep. 24, 2003  (JP)  ............... 2003-332533

(51) Int. Cl.
*A61B 5/05* (2006.01)
(52) U.S. Cl. ........................................ 600/407
(58) Field of Classification Search ........... 600/407, 600/465, 431, 420, 458
See application file for complete search history.

(56) References Cited

U.S. PATENT DOCUMENTS

| 6,083,168 | A  | * | 7/2000  | Hossack et al.  | 600/443 |
| 7,069,068 | B1 | * | 6/2006  | Ostergaard      | 600/420 |
| 2002/0183621 | A1 | * | 12/2002 | Pfeiffer et al. | 600/473 |
| 2003/0125624 | A1 | * | 7/2003  | Shiki           | 600/443 |
| 2004/0147032 | A1 | * | 7/2004  | Martin et al.   | 436/69  |
| 2004/0215081 | A1 | * | 10/2004 | Crane et al.    | 600/473 |
| 2006/0282236 | A1 | * | 12/2006 | Wistmuller      | 703/2   |

FOREIGN PATENT DOCUMENTS

| JP | 08-015439    | 1/1996  |
| JP | 2001-054520  | 2/2001  |
| JP | 2002-282248  | 10/2002 |
| JP | 2003-190148  | 7/2003  |
| JP | 2003-199715  | 7/2003  |

OTHER PUBLICATIONS

Koenig et al., "Perfusion CT of the Brain: Diagnostic Approach for Early Detection of Ischemic Stroke," Radiology, vol. 209, No. 1, Oct. 1996, pp. 85-93.

* cited by examiner

*Primary Examiner*—Long V Le
*Assistant Examiner*—Saurel J Selkin
(74) *Attorney, Agent, or Firm*—Nixon & Vanderhye PC

(57) ABSTRACT

There is provided a blood-flow analysis apparatus for analyzing the time intensity curve for each pixel or region of interest of time-series images collected by photographing a desired region of a sample over time with a medical modality by applying a tracer to the blood of the sample. The analysis apparatus includes a calculation unit for calculating parameters indicative of blood-flow dynamics peculiar to the measured tissue of the sample as ratio to or difference from parameters at a desired reference region on the basis of only the time intensity curve of the measured tissue, and a visual-information presentation unit for visually presenting the calculations by the calculation unit.

20 Claims, 10 Drawing Sheets

(EXAMPLE OF DIVISION INTO BLOOD-VESSEL CONTROL REGIONS)

(EXAMPLE OF 2D GRAPH OF BLOOD-FLOW ANALYSIS PARAMETERS)
(e.g. CBVratio vs. CBFratio IN MCA AREA)

(RISK MAP OF BLOOD-VESSEL CONTROL REGIONS)

(ANALYSIS PARAMETERS BY GAMMA FUNCTION FITTING IN DYNAMIC STUDY)

(TIC PARAMETERS OF HEALTHY PART AND DISEASED PART)

APPARATUS AND METHOD FOR ANALYZING BLOOD FLOW

BACKGROUND OF THE INVENTION

1. Field of the Invention

The present invention relates to an apparatus and a method for analyzing the blood-flow dynamics of a sample from image data of the sample obtained with medical diagnostic imaging apparatus such as a magnetic resonance imaging (MRI) scanner, an X-ray CT scanner, a single photon emission CT (SPECT) scanner, a positron emission CT (PET) scanner and, more particularly, it relates to an apparatus and a method for measuring blood-flow dynamics easily, quickly, and accurately using time-series continuous image data collected by applying a labeled substance which is called a tracer to the blood flow in the sample.

2. Description of the Related Art

In general, in dynamic study with an X-ray CT scanner or a dynamic susceptibility contrast MRI (DSC-MRI) with a magnetic resonance imaging scanner, as described in "Østergaard L, Sorensen A G, Kwong K K, Weisskoff R M, Gyldensted C, Rosen B R; High Resolution Measurement of Cerebral Blood Flow Using Intravascular Tracer Bolus Passages, Part II: Experimental Comparison and Preliminary Results, Magn Reson Med, 1996; 36:726-736" and "Østergaard L, Weisskoff R M, Chesler D A, Gyldensted C, Rosen B R; High Resolution Measurement of Cerebral Blood Flow Using Intravascular Tracer Bolus Passages, Part I: Mathematical Approach and Statistical Analysis. Magn Reson Med, 1996; 36:715-725," a contrast medium is infused through a vein to collect time-series image data, and then the images are analyzed to express blood-flow parameters in numerical form or images. An example of the analysis procedure is shown in steps S1, S2, S3A, and S4A or steps S1, S2, S3B, and S4B of FIG. 8.

For quantification, deconvolution with the time intensity curve (TIC) of a measured tissue, Ci(t), is performed with the TIC of an artery flowing into the tissue as input function to eliminate variations in pulmonary circulation and medium infusion, thereby obtaining the residue function: Ri(t) specific to the tissue, from which parameters such as blood flow: Flow, which is the index of blood-flow dynamics (cerebral blood flow: CBF for brains), mean transit time: MTT, blood volume: Volume (cerebral blood volume: CBV for brains) are calculated.

Another example is, as described in "Radiology 1998; 209 85-93" and "Miles K et al., British Journal of Radiology, 1991; 337: 643-645," a maximum gradient method of calculating Flow from the maximum gradient of tissue TIC: Ci(t) and the maximum value of Ca(t).

In general, only one of bilaterally symmetric organs, such as brains, kidneys, and lungs, often develops abnormality, in which case diseased organs or regions have been often compared to the other corresponding healthy organs or regions or relatively stable part of diseased organs up to now. The ratio to the healthy part (healthy-part ratio) or the difference from that (healthy-part difference) is used for comparison, which is limited only to the case of documentation in numerical form but not in image. Disease data is often stored in database as healthy-part ratio or healthy-part difference.

The principle and situation of conventional blood flow measurement including its problems will be described with reference to literature.

(Blood Flow Model)

FIG. 9 shows a blood flow model into which a contrast medium is applied. In the drawing, case 1 shows a case in which a bolus of a contrast medium is infused into an artery in the close vicinity of a tissue of the blood flow model, while case 2 shows a case in which the contrast medium is infused into a cubital vein.

The model of the blood flow is expressed mathematically as $$Ci(t)=Ca(t)*Ri(t)=\int_0^T Ca(T-t)Ri(t)dt \quad (1)$$

where Ca(t) is an artery TIC, Ci(t) is a tissue TIC, Ri(t) is a tissue MTF (modulation transfer function), and * is convolution.

Particularly, when Ca(t)=δ(t), where δ(t) is a delta function, the blood flow is expressed as $$Ci(t)=\delta(t)*Ri(t)=Ri(t) \quad (2)$$

Specifically, in case 1 in which a bolus of a contrast medium is infused into an artery in the close vicinity of a tissue, the tissue MTF: Ri(t) becomes Ci(t).

In the case of calculations of CBF, CBV, and MTT by the conventional deconvolution method, Ri(t) is obtained from Ca(t) and Ci(t), as shown in FIG. 8, from which the parameters are obtained by the equations $$CBF = \max \text{ of } [Ri(t)] \quad (3)$$

$$CBV = \int_0^\infty Ci(t)\,dt \Big/ \int_0^\infty Ca(t)\,dt$$

$$MTT = CBV/CBF$$

The conventional calculation method includes a case of measuring artery TIC and correcting tissue TIC with the artery TIC and a case of analyzing tissue TIC without measuring the artery TIC. In the former case, the absolute values of the blood flow parameters are obtained; in the latter case, relative indices which reflect the blood flow (depending on variations among individuals and the respiratory function) are obtained.

FIG. 10 shows a gamma function used in TIC analysis. The meanings of the parameters in the drawing are as follows:

a) PH: Peak Height
the maximum value of C(t) (T0≦t<Infinity)

b) PT: Peak Time
time from the base time to PH c) AC: Area under Curve
an area under the fitting curve, which corresponds to rCBV d) MT1: 1'st moment
time from the base time to the first moment (barycenter)

e) rFLOW: relative Flow
relative flow based on a centric volume theory, which includes effects of blurring in pulmonary circulation or an artery f) TT: Transit Time
time between inflection points of PH with PT interposed therebetween (different from a full width at half maximum (FWHM))

g) AT: Appearance Time
time from the base time until C(t) rises to a value $A_{AT}$ times as high as PH (default: $A_{AT}$=0.05)

h) DT: Disappearance Time
time from the peak time until C(t) falls to a value $A_{DT}$ times as high as PH (default: $A_{DT}$=0.4)

i) MT2: 2'nd moment
the second moment of the time of TIC, which corresponds to dispersion and indicates the temporal dispersion of the curve j) US: Up Slope slope at a rising inflection point k) DS: Down Slope.

slope at a falling inflection point l) PTE: effective Peak Time m) MT1E: effective 1'st moment, MT1E=MT1−AT time after the arrival of a contrast medium to a barycenter, MT1 with delay time in pulmonary circulation excluded n) rFLOWE: effective relative FLOW, rFlOWE=AC/MT1E closer to the true flow, with delay time in pulmonary circulation excluded When the respective Ca (t) of the arteries are different only in delay: Td (refer to FIG. 12), also the delay can be expressed as Ri(t−Td) in which Ri(t) contains Td.

Ri(t) can be obtained by the expression of Fick $$dCi(t)/dt = f \bullet \{Ca(t) - Cv(t)\} \quad (4)$$

where Ci(t) is tissue TIC, Ca(t) is input artery TIC, Cv(t) is output vein TIC, and f is blood flow (flow rate in unit volume [ml/cc/sec])

and the integral is expressed as $$Ci(t) = f\left\{ \int_0^t Ca(s)\,ds - \int_0^t Cv(\bar{s})\,ds \right\} \quad (5)$$

where, when Ca(t)=δ(t), Ci(t)=Ri(t) holds.

Accordingly, the following expression holds:

$$\int_0^t \delta(s)\,ds = \text{Ramp}(t)$$

where Ramp(t)=1:t>0,=0: otherwise, therefore the following expression holds:

$$Ri(t) = f\left\{ \text{Ramp}(t) - \int_0^t Cv(s)\,ds \right\} \quad (6)$$

Unless artery TIC: $Ca_n(t)$ in the cross vicinity of the inflow of the object tissue is measured, true MTT cannot be calculated normally.

When a contrast medium is infused through a cubital vein (case 2), TIC: Ca(t) of an artery flowing into the tissue expands in terms of time owing to pulmonary circulation. Thus both tissue TIC: Ci(t) and vein TIC: Cv(t) expand as compared with case 1. The difference for positions of cerebral arteries after the contrast medium has flowed into a brain from a lung is only delay but the width is substantially fixed if arteries of different flow channels do not join together but branch off.

There can be several kinds of Ri(t) depending on the model of blood flow.

For example, in the case of a box model, Ri(t) is expressed as

Ri(t)=f: Td<t<Td+MTT,=0: otherwise for an exponential model, Ri(t) is expressed as Ri(t)=f*exp[−(t−Td)/MTT]:Td<t<Td+MTT, =0:otherwise (Relationship between Tissue MTT and Barycentric Time MT1)

Problems of using the barycenter time MT1 of the first pass of tissue TIC as index will be examined.

Although the time between the MT1 of Ca(t) and Cv(t) has no dependence to Ri(t), or the blood flow model, the MT1 of Ci(t) has dependence to the blood flow model. When tissue TIC: Ci(t) and any artery TIC: Ca(t) are measured, the following expression holds:

$$MTT = a(MT1i - MT1a - Td) \quad (7)$$

where MT1$i$ and MT1$a$ are the respective barycenters of the first passes thereof and Td (refer to FIG. 12) is the delay time from the measured artery to the inlet.

Where a is a coefficient which depends on the model and will fall within the range of $1 \leqq a \leqq 2$. For a plug-flow contrast medium, the blood flow is of a box model in which a=2 holds; for a diffusion tracer, the blood flow is of an exponential model, in which a=1 holds.

Letting MT1$v$ be the barycentric time for a vein, one obtains $$MTT = MT1v - MT1a - Td \quad (8)$$

Briefly, there is a difference of two times between the times from the inlet of the capillary vessel to the respective barycenters of the tissue and the vein (refer to FIG. 10). This is based on a model in which the response function of the tissue is of a box type.

The barycentric time MTT of TIC: C(t) is generally calculated by $$MTT = \int_0^\infty tC(t)\,dt \bigg/ \int_0^\infty C(t)\,dt \quad (9)$$

As described in Meier P, Zierler. K et al., "Journal of APPLIED PHYSIOLOGY" Volume 6, June 1954, 731-744, the definition by Zierler, "the output region from a tissue, i.e. the barycenter of TIC in a vein is defined MTT," that is, $$MTT = MT1v \quad (10)$$

is a definition in the case where the time that a contrast medium is rapidly infused into the inlet of a capillary wall in the tissue is assumed to be zero (case 1 in FIG. 9)

In the case where a contrast medium is infused through a cubital vein (case 2 in FIG. 9) as in an actual inspection, for example, when Ca(t) is measured at a carotid artery, Td varies with tissues depending on the control blood vessel of the brain and inputted Ca(t) expands during pulmonary circulation. Accordingly, the expression of Zierler cannot be used in its form.

The vein TIC has not model dependence but the tissue TIC has model dependence for the barycentric time, in both of which the barycenter of the artery TIC must be determined for quantification.

(Calculating CBF, CBV, and MTT by Maximum Gradient Method)

(Principle of Maximum Gradient Method)

As has been described, the expression of Fick is expressed as $$dCi(t)/dt = f \bullet \{Ca(t) - Cv(t)\} \quad (11)$$

wherein when the time of interest is time before the contrast medium flows into a vein and is shorter than the mean transit time of the tissue, or t<MTT, the following expression holds:

$$Cv(t) \cong 0 \quad (12)$$

Thus, the expression of Fick becomes $$dCi(t)/dt = f \cdot Ca(t) \quad (t < MTT) \tag{13}$$

When formula (13) is further differentiated by time, it is expressed as $$d^2Ci(t)/dt^2 = f \cdot dCa(t)/dt \tag{14}$$

As shown in FIG. 11, at time $t = t_{max.grad.}$ when Ci (t) has the maximum slope at rise time, formula (14) becomes $$d^2Ci(t_{max.grad.})/dt = 0$$

from the relation f>0, the right side of formula (14) becomes $$dCa(t_{max.grad})/dt = 0$$

Since TIC is an upward convex curve, Ca(t) becomes a maximum value: $Ca_{max}$ at $t = t_{max.grad}$. Thus the following relation holds:

$$Ca(t_{max.grad}) = Ca_{max}$$

formula (13) is thus transformed to calculate blood flow f by the expression $$f = \{dCi(t_{max.grad})/dt\}/Ca_{max} \tag{15}$$

The maximum gradient method is based on the assumption that no contrast medium flows into a vein at $t = t_{max.grad}$. Accordingly, the assumption does not hold when the time width of a bolus infusion (input artery of the tissue) of input function is long. Accordingly, the assumption failure cannot sometimes be ignored for patients of poor pulmonary circulation. Even if Ci(t) and Ca(t) have delay time (refer to FIG. 12), $Ca_{max}$ is not influenced by the delay time. Since CBF is calculated by the maximum gradient of TIC, the influence of the delay time is smaller than that by the method of calculating CBF from MTT and CBV without taking in consideration of the influence of delay time.

Also the deconvolution method used in the actual X-ray CT scanners in which Ca(t) is measured to obtain the response function of a tissue cannot ignore the influence of the delay time. They both have their own advantages and disadvantages case by case.

$dCi(t_{max.grad})/dt$ can be calculated as the first inflection point when it is approximated by gamma-variate function (refer to FIG. 10).

(Summary)

It is therefore difficult in DSC-MRI to measure artery TIC: Ca(t) accurately because linearity between index deltaR2* and the intensity of a contrast medium has not been proved and so high-intensity medium cannot ensure a dynamic range because of noises. With the reported "deconvolution method", unless measured artery TIC: Ca(t) is in the close vicinity of a control tissue, the delay time (refer to Td of FIG. 12) from the measured region to the tissue is not corrected sufficiently, thus causing an error.

Although the method of obtaining the absolute value of blood flow by the maximum gradient method is easier than the centroid method, it needs the measurement of artery TIC: Ca(t), having many conditions that the time width of Ca(t) must be shorter than tissue MTT and as such, the quantitativity is questioned.

SUMMARY OF THE INVENTION

The present invention is made to solve the above-described problems. Accordingly, it is a principal object of the invention to provide an apparatus and a method for analyzing blood flow capable of providing indices indicative of blood-flow dynamics quantitatively without measuring the artery TIC of a sample.

While the invention is applicable also to images taken from other modalities, as in dynamic analysis by X-ray CT scanners, it is another object dependent on the principal object of the invention to provide a blood-flow analysis apparatus capable of providing indices indicative of blood-flow dynamics quantitatively without measuring artery TIC using images taken from a dynamic susceptibility contrast MRI (DSC-MRI) scanner.

It is yet another object of the invention to provide a blood-flow analysis apparatus capable of not only expressing healthy-part ratios or healthy-part differences using the indices as values for a region of interest but also positively expressing them as images by the apparatus.

It is still another object of the invention to provide a blood-flow analysis apparatus capable of providing information necessary for treatment quickly, thereby supporting diagnosis through treatment.

According to an embodiment of the invention, in order to achieve the above-described objects, there is provided a blood-flow analysis apparatus for analyzing the time intensity curve (TIC) for each pixel or region of interest of time-series images collected by imaging a desired region of a sample over time with a medical modality by applying a tracer to the blood of the sample. The analysis apparatus includes a calculation unit for calculating parameters indicative of blood-flow dynamics peculiar to the measured tissue of the sample as ratio to or difference from parameters at a desired reference region on the basis of only the time intensity curve (TIC:Ci(t)) of the measured tissue, and a visual-information presentation unit for visually presenting the calculations by the calculation unit.

For example, the calculation unit uses the parameters of a region that is regarded as a healthy part of the photographed image as the reference region, wherein, if the desired region is a bilaterally symmetrical organ, the reference region is a healthy region of the pair and, if the desired region is a brain, the reference region is a substantially stable region irrespective of sample, or a phantom with a known flow rate.

Preferably, the calculation unit calculates the parameters: blood flow (FLOWratio) based on the ratio of the rising maximum gradient (US) of the time intensity curve (TIC: Ci (t)) of the tissue to the rising maximum gradient (USref) of the time intensity curve of the reference region; blood volume (VOLUMEratio) based on the ratio of the area under curve (AC) of the time intensity curve (TIC: Ci(t)) of the tissue to the area under curve (ACref) of the time intensity curve of the reference region; and a mean transit time (MTTratio) based the relation expression, MTTratio=VOLUMEratio/FLOWratio.

Preferably, the calculation unit calculates the parameters: the difference (deltaMTT) in mean transit time (MTT) based on the difference between the barycenter (MT1) of the time intensity curve (TIC: Ci(t)) of the tissue and the barycenter (MT1ref) of the reference region and a coefficient (a) depending on the model; and a blood volume (VOLUMEratio) based on the ratio of the area under curve (AC) of the time intensity curve (TIC: Ci (t)) of the tissue to the area under curve (ACref) of the reference region.

Preferably, the calculation unit includes an absolute-value calculation unit capable of calculating the absolute values of the parameters calculated by the calculation unit for each pixel or region of interest when absolute values which are the quantitative values of the parameters of the reference region are given.

In order to achieve the above-described objects, by a blood-flow analysis method according to the invention, in analyzing the time intensity curve (TIC) for each pixel or region of interest of time-series images collected by photographing a desired region of a sample over time with a medical modality by applying a tracer to the blood of the sample, only the time intensity curve (TIC: Ci(t)) of the tissue of the sample is measured, parameters indicative of blood-flow dynamics peculiar to the measured tissue are calculated as ratio to or difference from parameters at a desired reference region on the basis of the time intensity curve (TIC: Ci(t)) of the measured tissue, and the calculations are visually presented.

The invention relates to an apparatus and a method for quantifying blood-flow parameters using a tracer for the blood flow of a sample, wherein indices for quantifying blood-flow parameters are provided without measuring artery TIC. Quantification indices used in the invention include ratio to or difference from a specified reference region of a measurement object or a fluid phantom. Specifically, the invention provides (a) a method of calculating the temporal difference in MTT, deltaMTT, from barycentric time MT1 of tissue TIC: Ci(t) and (b) a calculation method of using the ratio of maximum slope US by a maximum gradient method. When the absolute values of the parameters of a reference region are given, also the CBF, CBV, and MTT can be converted to their absolute values.

The quantification of blood-flow parameters according to the invention eliminates the necessity for artery measurement, thus allowing easy and quick quantification, which is particularly effective in treating diseases that require an urgent remedy, such as cerebral infarction. The values of analysis according to the invention is, principally, quantitative values, ratio to or difference from a reference region. This provides the following advantages: Since the most of measurements of blood flow by various modalities are ratios and differences and have been stored as database and also the invention provides information of ratios and differences, the data stored in the database can easily be compared to that of the invention. When information of parameters that can be quantified are given, irrespective of whether the reference region is a tissue in an object patient or a blood-flow mimic phantom, the blood-flow parameters of the tissue can be converted to the absolute values and then the absolute values can be mapped.

Since information is provided with organic relationship between the acquired blood-flow information of individual object patients and a stored disease database by the apparatus, not only diagnosis but also treatment can be performed quickly and accurately.

Cerebral infarction and myocardial infarction, which are now the second and third principal causes of death in the world, require blood-flow information most, and thus it is required to read other biological information or image information outputted from a diagnostic imaging apparatus accurately and to make a diagnosis for medical treatment. The apparatus and a method of analyzing blood flow according to the invention can surely meet the needs.

DESCRIPTION OF THE PREFERRED EMBODIMENTS

A blood-flow analysis apparatus according to an embodiment of the present invention will be described with reference to the drawings.

The blood-flow analysis apparatus acquires information on blood-flow dynamics from image data collected by a dynamic study method with medical modality such as a magnetic resonance imaging scanner or an X-ray CT scanner and displays it. Accordingly, the blood-flow analysis apparatus is preferably in an environment where such image data can be acquired and may be integrated with or separated from medical modality. With a separate structure, collected image data is sent from medical modality to a blood-flow analysis apparatus via a recording medium or a communication unit.

Figure 1:
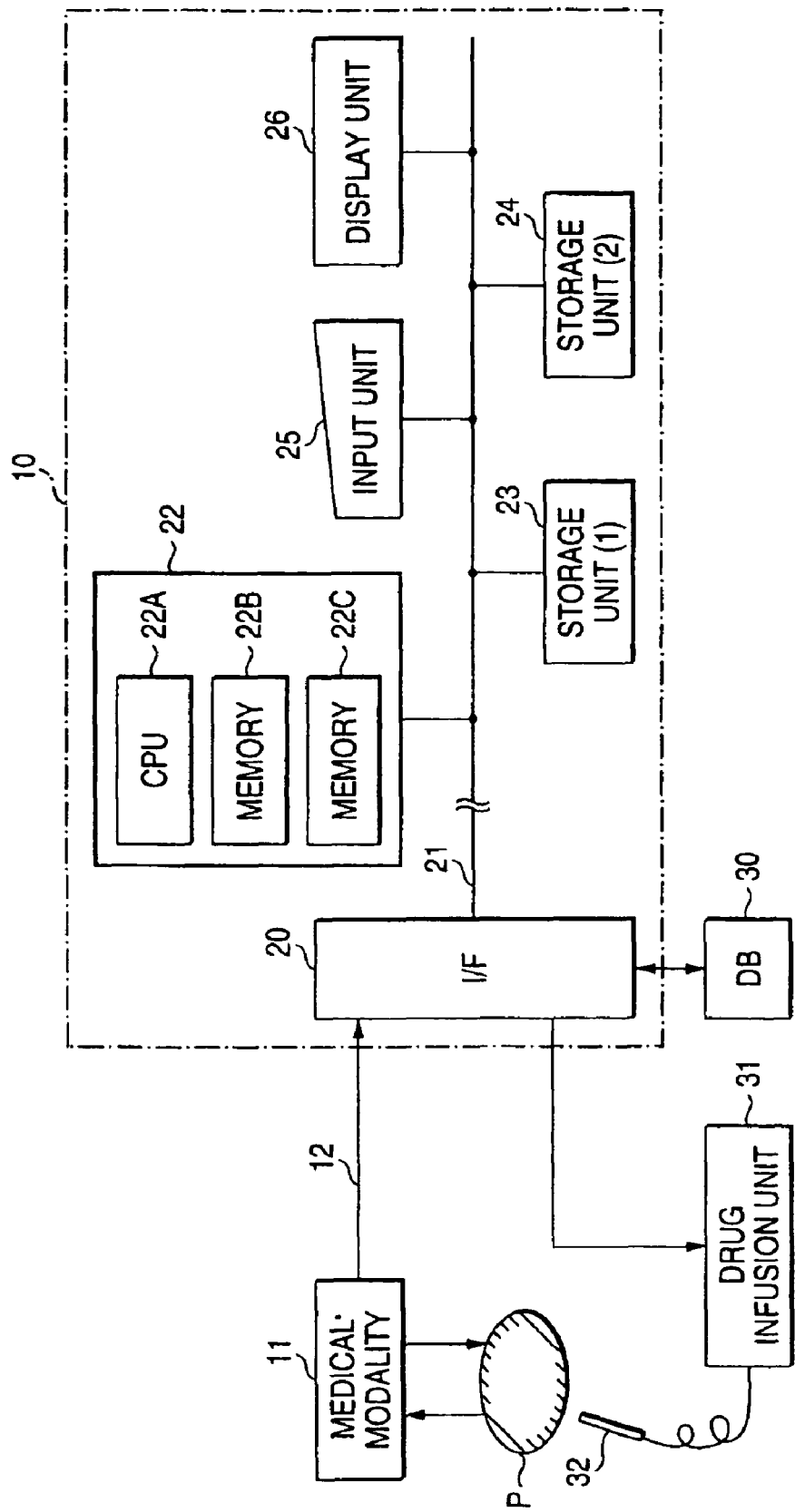
FIG. 1 is a schematic block diagram of a blood-flow analysis apparatus according to an embodiment of the present invention.

FIG. 1 shows the general outline of the blood-flow analysis apparatus according to the embodiment. The blood-flow analysis apparatus 10 receives image data of a sample P collected by a medical modality, which is imaged by a dynamic study method, via a communication unit 12 (or a recording medium).

Specifically, the blood-flow analysis apparatus 10 includes an input/output interface (I/F) 20. The interface 20 connects to a bus 21. The bus 21 connects to an arithmetic processor 22 for arithmetic computations, storage units 23 and 24 for storing necessary information such as data and programs, an input unit 25 for an operator to input desired information manually, and a display unit 26 for displaying images. Of the storage units 23 and 24, the storage unit 23 stores image data sent through, e.g., the communication unit 12, while the storage unit 24 stores programs and fixed data necessary for analyzing blood flow in the arithmetic processor 22 in advance.

The arithmetic processor 22 includes a CPU 22A and memories 22B and 22C. The arithmetic processor 22 stores programs read from the storage unit 24 in the memory 22B and so performs the following blood-flow analysis in accordance with the programs. The memory 22C temporarily stores data that generates during the process of the CPU 22A.

The blood-flow analysis apparatus 10 also connects to a database (DB) 30 to which analyses can be written and a drug infusion unit 31 which is used by a doctor at treatment. The drug infusion unit 31 can infuse a therapeutic drug into the sample P through a catheter 32.

The process of blood-flow analysis performed by the blood-flow analysis apparatus 10 will be described hereinbelow. The process will be described for each paragraph from the general outline and the theory of the analysis through the process and the display in order to avoid complicated explanation.

(1. Outline of the Analysis)

The ratio to or difference from a reference region of a measuring object will be used as the quantitative indices of the blood-flow dynamics used in this embodiment. Specifically speaking, the methods are a method (a) of calculating the temporal difference deltaMTT between barycentric times MT1 and MTT of tissue TIC: Ci(t) (a calculation method by a centroid method) and a method (b) of using the ratio of slope US by a maximum gradient method (a calculation method by a maximum gradient method).

The calculation method (a) by a centroid method and the calculation method (b) by a maximum gradient method which are keys of the present invention will be described hereinbelow on the basis of the principle of conventional blood-flow measurement. Then a method for forming another map using data acquired from the calculation will be described. Furthermore, a method for forming the map of the absolute values of a reference region using the absolute values of a reference region will be described, which uses the fact that, of the parameters, CBF, CBV, and MTT of the reference region, given at least two absolute values, the three parameters can be converted to absolute values according to the relation CBV=MTT·CBF.

It is a fact that obtained blood-flow parameters are also quantitative values that can be compared among patients and diseases irrespective of medical modality. Accordingly, what is called a computer aided diagnosis (CAD) will also be described in which the blood-flow parameters are compared to data stored as database to allow clear placement of patient data at that point in time.

(2. Calculating Quantification Indices)

The calculation of the difference in MTT: deltaMTT by the centroid method and the method for determining the healthy-part ratio of CBF, CBV, and MTT by the maximum gradient method according to the invention will be described, which are quantification indices calculated without using new artery TIC. Of the two physical quantities, CBV is common to both the methods but MTT and CBF are different in calculation method.

(2.1 Calculating Difference in MTT: deltaMTT by Centroid Method)

The fact that the true ratio of CBV: CBVratio between a diseased part and a healthy part and the difference in MTT: deltaMTT can be calculated without measuring an artery will be described first.

The TIC parameters of the healthy part are indicated with subscript h as follows:

Healthy part: $Ca_h(t)$, $Ci_h(t)$ $MT1a_h$, $MT1i_h$, $MT1Ea_h$, $MT1Ei_h$

Diseased part: $Ca(t)$, $Ci(t)$ $MT1a$, $MT1i$, $MT1Ea$, $MT1Ei$

Assuming that a tissue blood-flow model is a box model, the absolute value: deltaMTT of the difference in MTT between the diseased part and the healthy part is calculated by the expression $$\text{delta}MTT = \alpha(MT1Ei - MT1Ei_h) \quad (16)$$

However, it is assumed that the artery TIC does not broaden (the half band width does not vary). Even when delay time until a contrast medium reaches a tissue varies in an artery because of collateral circulation, the artery TIC will not vary unless arteries are joined together.

Note that the healthy-part ratio of MT1E cannot be cancelled and so cannot be the absolute value even if the broadening of Ca(t) is the same. Also, if the artery TIC is equal at the healthy part and the diseased part (without collateral circulation, however, which will be difficult in infarction), the absolute value can be calculated as follows from the difference in barycentric time which is not corrected by appearance time AT:

$$\text{delta}MTT = \alpha(MT1i - MT1i_h) \quad (17)$$

The true CBV ratio between the diseased part and the healthy part is the ratio of area under curve AC, as follows:

$$CBVratio = CBV/CBV_h$$
$$= \left\{ \int_0^\infty Ci(t)\,dt \Big/ \int_0^\infty Ca(t)\,dt \right\} \Big/ \left\{ \int_0^\infty Ci_h(t)\,dt \Big/ \int_0^\infty Ca_h(t)\,dt \right\}$$

The time quadrature of artery TIC may be assumed to be equal even with delay unless a contrast medium leaks in partway. The expression is as follows:

$$\int_0^\infty Ca(t)\,dt = \int_0^\infty Ca_h(t)\,dt$$

Accordingly, the following expression is given:

$$CBVratio = AC/AC_h \quad (18)$$

<Deriving deltaMTT>

The true MTT can be defined as

Diseased part: $MTT = \alpha(MT1i - MT1a - Td)$,

Healthy part: $MTT_h = \alpha(MT1i_h - MT1a_h - Td_h)$

Here the difference deltaMTT in MTT between the diseased part and the healthy part is calculated as follows:

$$\text{delta}MTT = MTT - MTT_h = \alpha(MT1i - MT1a - Td) - \alpha(MT1i_h - MT1a_h - Td_h)$$

$$Td_h = ATi_h - ATa_h, \; Td = ATi - ATa$$

Accordingly, the following expression is given:

$$\text{delta}MTT = \alpha(MT1 - MT1a - (ATi - ATa)) - \alpha(MT1i_h - MT1a_h - (ATi_h - ATa_h))$$

Assume that the broadening of TIC of input artery in the close vicinity of a region of interest is equal at a healthy part and a diseased part as follows (the assumption can hold unless an artery with different delay joins with the input artery):

$$MT1Ea = MT1Ea_h$$

then the expression holds:

$$MT1a - ATa = MT1a_h - ATa_h$$

Accordingly, the expression holds:

$$\text{delta}MTT = \alpha(MT1i - ATi) - \alpha(MT1i_h - ATi_h)$$

By the definition of parameters, the following expression holds:

$$MT1Ei_h = MT1i_h - ATi_h, \quad MT1Ei = MT1i - ATi$$

Consequently, the following expression is given:

$$\text{delta}MTT = \alpha(MT1Ei - MT1Ei_h) \tag{19}$$

In other words, the difference in MTT of a certain part from the healthy part can be expressed by a coefficient multiple of the difference in MT1E, time from appearance time to barycentric time MT1.

Assuming that the delay in TIC of the input arteries in the close vicinity of a healthy-part tissue and a diseased-part tissue is equal, $ATi = ATi_h$ holds, in which case the appearance time AT may not be taken into consideration. Thus, the expression is as follows:

$$\text{delta}MTT = \alpha(MT1i - MT1i_h) \tag{20}$$

As has been described, coefficient a has model dependence and will fall within the range $1 \leq \alpha \leq 2$, but will not vary depending on tissues and can be determined uniquely. When coefficient a is determined to a fixed value by experiment etc., deltaMTT can be calculated.

To calculate deltaMTT, it is also possible to use peak time: PT which is the time that TIC becomes the maximum approximately or PTE (=PT−AT) which is obtained by subtracting appearance time AT from PT, in place of MT1E and MT1. With PTE or PT in place of MT1, an error arising when TIC can be analogous to a bilaterally symmetric shape is not so large that deltaMTT can be surely obtained without being affected by recirculation etc. On the other hand, with MT1, when recirculation is included in the calculation, an error may arise. Accordingly, either will do for practical purpose.

Expression corresponding to formulas (19) and (20) for PT is as follows:

$$\text{delta}MTT = \alpha(PTEi - PTEi_h) \tag{21}$$

$$\text{delta}MTT = \alpha(PTi - PTi_h) \tag{22}$$

(2.2 Healthy-Part Ratio of CBF, CBV, and MTT by Maximum Gradient Method)

A method for calculating the ratios of CBF, CBV, and MTT to the reference values even without measuring artery TIC but with a maximum gradient value of tissue TIC by the maximum gradient method will be described.

Even with delay time in a cerebral blood vessel, the peak value $Ca_{max}$ of Ca(t) will be equal in the entire object organ in one inspection. Accordingly, for the comparison of two regions in one inspection, $Ca_{max}$ disappears. The difference between different examinations or a difference due to patient's cardiac and pulmonary functions amounts to the difference in $Ca_{max}$. Accordingly, the healthy-part CBF ratio: CBFratio calculated by the maximum gradient method is expressed by subscript h, the following expression is given:

$$\begin{aligned}CBFratio &= CBF/CBF_h \\ &= [\{dCi(t_{max.grad})/dt\}/Ca_{max}]/[\{dCi(t_{max.grad})/dt\}_h/Ca_{max}] \\ &= \{dCi(t_{max.grad})/dt\}/\{dCi(t_{max.grad})/dt\}_h \\ &= US/US_h = USratio\end{aligned} \tag{1}$$

Thus USratio becomes equal to the ratio of CBF which is an absolute value.

Since DSC-PI needs less contrast medium than CT-PI (approximately 20 to 50% of CT-PI), bolus infusion can be decreased. This increases the possibility that flowing to a vein, which is an important condition of the method of this embodiment, is negligible.

Also, healthy-part CBVratio and healthy-part MTTratio can be calculated by the following expressions:

CBVratio can be written as:

$$CBVratio = CBV/CBV_h = AC/AC_h = ACratio \tag{23}$$

MTTratio can thus be written as:

$$MTTratio = CBVratio/CBFratio = ACratio/USratio \tag{24}$$

In summary, the absolute value ratios of CBF, CBV, and MTT can be calculated by the expressions using only the curve parameters of tissue TIC.

CBFratio = USratio

CBVratio = ACratio $$MTTratio = ACratio/USratio \tag{25}$$

(3. Determining Reference Region)

The reference region may be a region that has relatively low frequency in disturbance of blood circulation and high probability of normality such as the cerebellum of one patient or, alternatively, for a pair of left and right organs, such as brains, one of which is generally damaged, a normal corresponding region.

The values calculated by the method of the present invention are indices using the ratio to and difference from specified references and also quantitative values. In other words, they can be compared among patients and measurements in one apparatus or different apparatuses and also compared to other modalities such as X-ray CT scanner, SPECT, and PET. The results are not only expressed numerically for a region of interest (ROI) but also, with DSC-MRI, variations in intensity due to gains or coil sensitivity for multisliced whole brains can be offset by taking on the ratio to a base image. The expression is as follows:

$$\text{delta}R2^*(n) = \ln[S_{base}/S(n)] \quad (n=1, 2, \text{---} N)$$

This allows mapping of ratios and differences, which is proposed in the invention, for each voxel in the whole brain, with a certain sliced or extracted region as reference.

Figure 2:
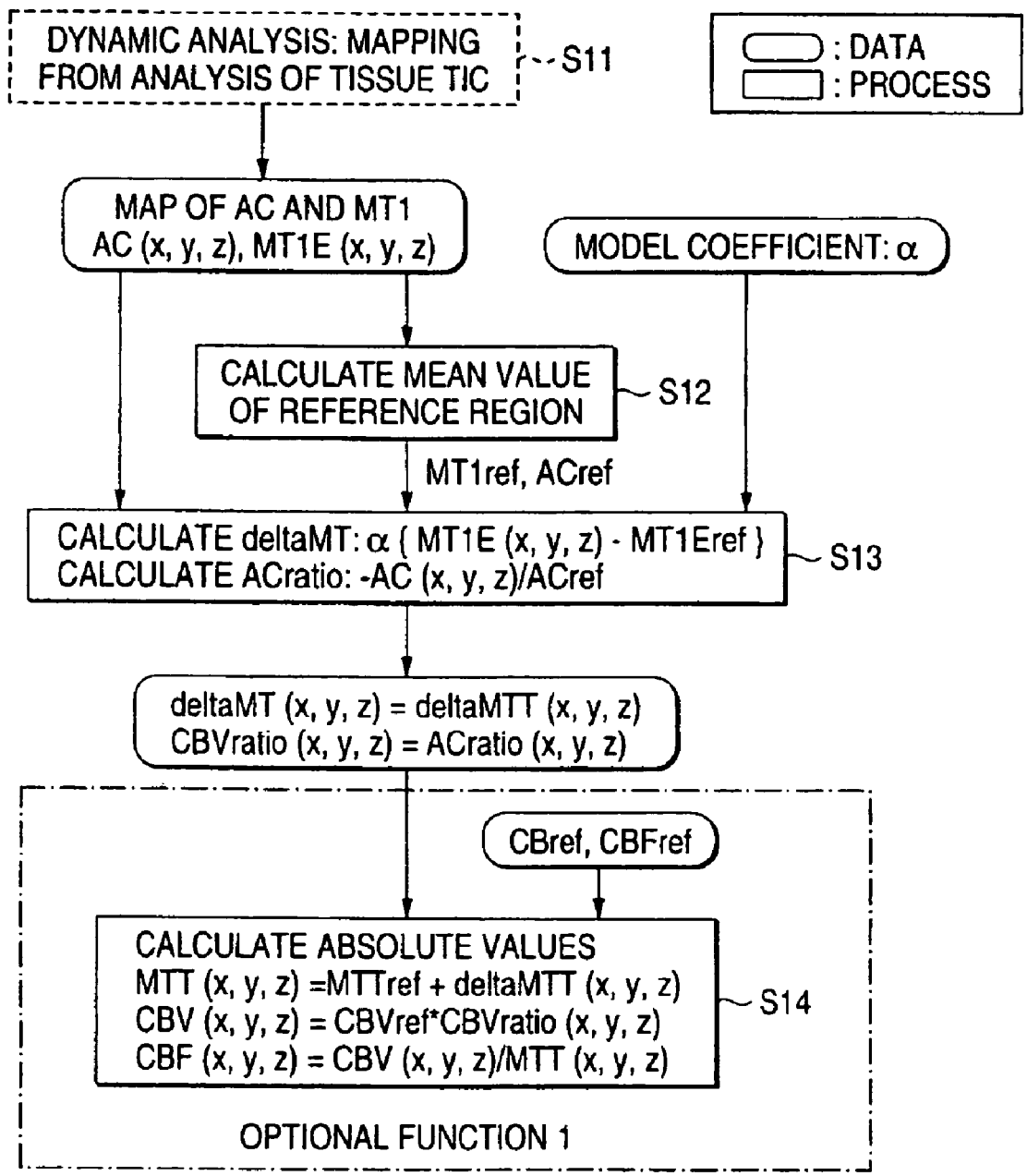
FIG. 2 is a schematic flowchart for the quantification process of blood flow parameters based on a centroid method which is executable in the embodiment.
Figure 3:
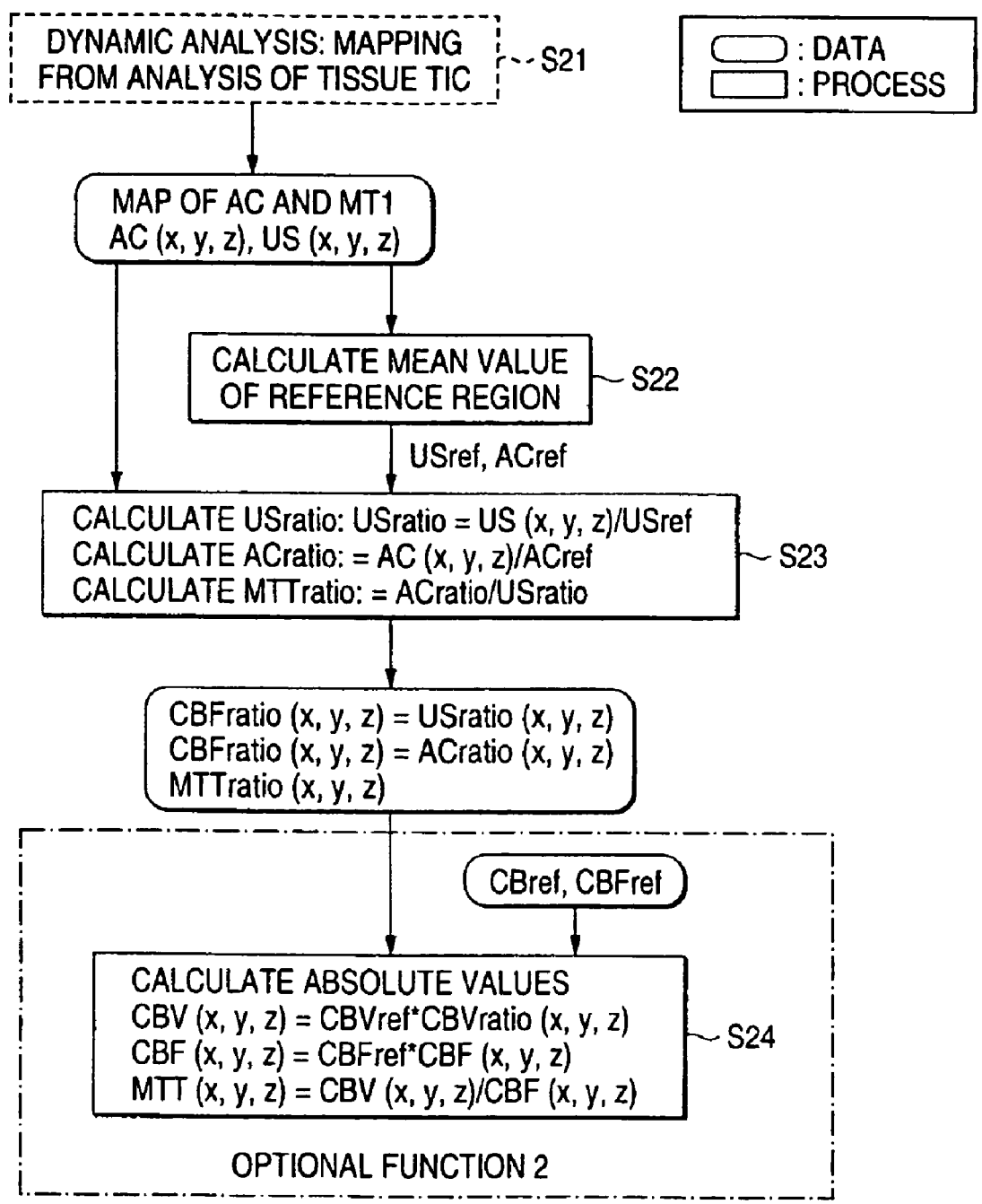
FIG. 3 is a schematic flowchart for the quantification process of blood flow parameters based on a maximum gradient method which is executable in the embodiment.

When the reference region has no individual difference, also the absolute values of blood-flow parameters can be calculated (refer to the optional functions in FIGS. 2 and 3). The reference region may be any region of a healthy part. A cerebellum is used frequently because it is relatively stable even if diseased, such as cerebral infarction. Ideally, it is the optimum not to take a patient' tissue but to image the phantom of which the values of blood flow are known, and to use the values as reference.

The ROI serving as reference may be set manually or may be set on a parameter map after dynamic analysis process. Alternatively, it may be set on a T1W or T2W image which is taken in advance.

When a reference region is set in advance on T1W or T2W collected before dynamic collection with an electronic position indicator (EPI) by perfusion measurement, the reference ROI can easily be set in terms of spatial resolution and also analysis proceeds automatically from dynamic collection without interruption to final mapping. This also facilitates automatic extraction of ROI, without the need for manual setting.

In setting the reference region at a healthy part, it can be sometimes predicted whether the healthy part is on the left or right, but it is generally unknown before inspection. The function of automatically extracting the reference region from image information by a doctor or with an apparatus will be described. It can be determined from the image of blood flow to be analyzed or the MRA image of blood vessels taken before the image of the blood flow is photographed.

The object of determination from the image of blood flow is limited to cerebrovascular diseases. Since a healthy part generally has large Flow and short MTT, the mean of the left and right of US map indicative of Flow is taken, of which the larger is determined to be a healthy part or the smaller of PT or MT1 map is determined to be a healthy part. AC cannot be used because it is indefinite which part is large. The use of the parameter of an analysis object depending on the method, specifically, the use of MT1 map or PT map for the centroid method of FIG. 2, to be described later, or US map for the maximum gradient method of FIG. 3, to be described later, allows calculation with the minimum input data. In determination from the blood-vessel image of MRA, when clogging occurs in either of the left and right arteries, the blood vessel from that point on is not imaged. Accordingly, it is determined such that, for example, an MIP image is divided by a lateral median line and the mean value is found, of which the larger is a healthy part. Alternatively, since the shapes of main arteries are known, for example, brains are searched for from the upstream internal carotid artery toward the left and right peripheral blood vessels to determine the length of passes which are regarded as vessels of a specified threshold or more. This allows the state of each branch to be grasped, allowing higher accurate determination than the mean value.

Figure 4:
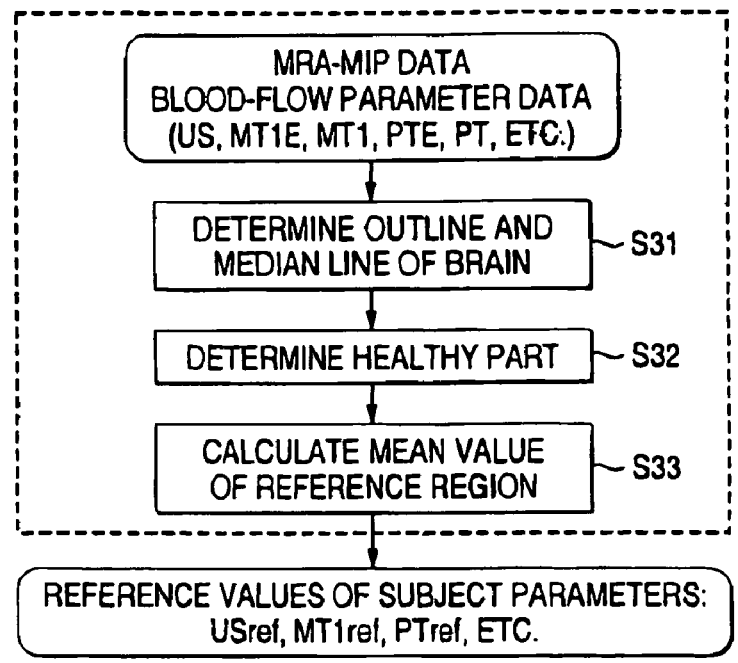
FIG. 4 is a schematic flowchart for the process of forming reference values of object parameters necessary for calculating absolute values in quantification of blood flow parameters.

Although a doctor may determine which of the left and right is a healthy part and input it to software in the subsequent stage, if it is determined automatically and then sent to the subsequent software, speedups are possible. In either case, the extracted region is used in common with multiple parameters of the analysis object. MRA may be carried out by either a TOF method or a PC method. When it is used for an image of a positioning plan to be imaged initially, the region can be determined at that stage. FIG. 4 shows a specific example of a reference-region mean-value calculating section.

(4. Analysis Process Flow)

Many software packages have been used for analyzing tissue TIC for individual ROI or pixel without measuring a general artery TIC to calculate parameters and map them. In this embodiment, two process flows of calculating quantification parameters using a map obtained by analyzing tissue TIC as input and mapping them are shown in steps S11 to S14 of FIG. 2 and steps S21 to S24 of FIG. 3, respectively. The processes of FIGS. 2 and 3 are executed, for example, selectively by the arithmetic processor 22.

FIG. 2 shows calculation of deltaMTT by the centroid method and calculation of the absolute values of blood-flow parameters MTT, CBV, and CBF, which are determined from the map of AC and MT1E resulting from the TIC analysis. Approximately, in place of barycentric time MT1E, they may be determined from MT1 with no regard for the AT, PTE with regard for AT of peak time, or PT with no regard for AT of peak time. FIG. 3 shows calculation of blood-flow parameters CBV, CBF, and MTT by the maximum gradient method and calculation of the absolute values thereof, which are determined from the map of AC and MT1 resulting from the TIC analysis.

Although the process of this embodiment is started on the basis of the map obtained by analyzing tissue TIC, it is to be understood that processes from data collection through collected-data analysis and representation to storage can be performed. Since a blood-flow map stored by general dynamic analysis can be called up from the database 30 etc. and subjected to quantification, it is very significant in making use of the past data. To form a through flow without interruption, the reference ROI is preferably determined on the image of other parameters before dynamic collection, as shown in paragraph 3, or processed automatically.

In step S12 of FIG. 2 and step S22 of FIG. 3, the mean values (absolute values) in the reference region are given. Specifically, the process of determining the mean values is performed as shown in step S31 (determining the outline and the median line of brains), step S32 (determining a healthy part), and step S33 (calculating the mean values of the reference region) of FIG. 4. The mean values are set on the maps of AC and MT1 for ROI or with the T1W image in advance before photographing and are read automatically at processing.

Thus providing the absolute values of a reference region as optional function offers a mode of calculating the absolute values of CBF, CBV, and MTT for each ROI or pixel (absolute-value calculating function). The absolute values of a reference region are generally taken for a normal region. Accordingly, statistics by age or sex which have been obtained by other modalities such as PET, SPECT, X-ray CT, and dynamic-CT scanners can be stored as data in the form of table or functions in advance and as such the absolute values can be calculated from the information such as the age and sex of an object patient. The absolute-value calculating function may be installed as standard function not as optional function.

(5. Statistical Analysis and Display of Result)

Figure 5:
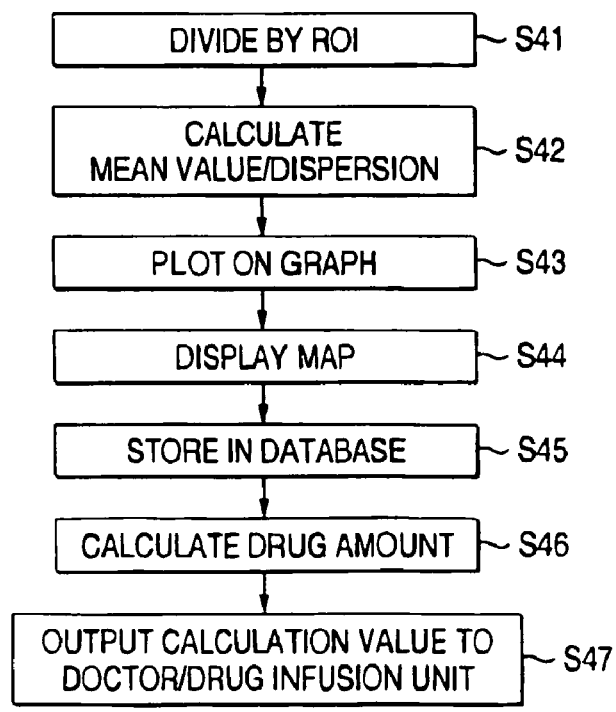
FIG. 5 is a partial flowchart for the process of displaying and presenting analyses executed in the embodiment.

Although the above-described four paragraphs relate to the flow to the mapping with quantification indices, this paragraph describes the function of performing statistical process with a quantification map and displaying the result on a graph or in image (map), and finally storing it in the database of blood-flow dynamics. The process is carried out by the arithmetic processor 22, part of which is shown in FIG. 5.

The map of quantified indices or numerical data can be one obtained without using the method of the invention. Thus the above-described function may be regarded as independent function.

Brains have a controlled region for each blood vessel. Thus the invention includes (a) a function of dividing controlled region by ROI (step S41 in FIG. 5), (b) a function of calculating mean values/dispersion for each divided ROI (step S42), (c) a function of plotting them on a graph for each divided region of a specified patient (step S43), and (d) a function of displaying them as a map (step D44). The contents of the display are stored in the database 30 together with numerical data indicative of the analyses (step S45).

Figure 6A:
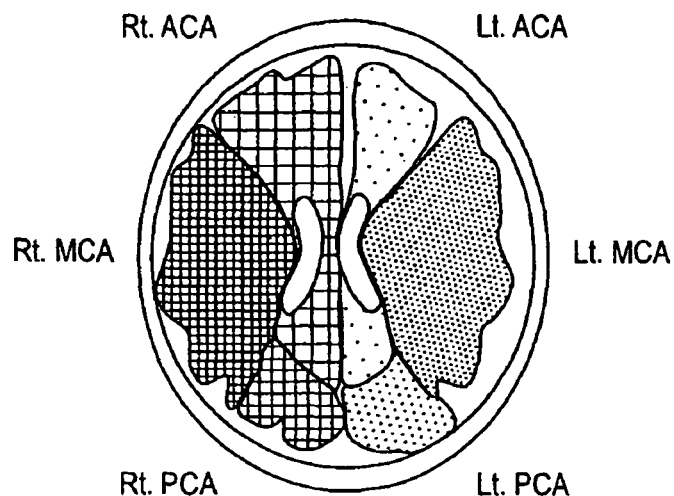
FIG. 6A is a diagram of an example of a display adopted in the embodiment.

The ROI division of (a), for example, two-dimensional slicing is performed as shown in FIG. 6A. Multislicing can be performed in three dimensions. In division by blood flow, brains can be divided into, e.g., six regions because the main vessels include three kinds of MCA, ACA, and PCA in pairs or a total of six vessels. The brains can be further divided finely because each vessel branches off. Since brains vary for each patient, they are transformed to standard brains and then overlapped with the dividing pattern of a template. This allows atomization. In that case, conversely, ROI which has been divided according to the standard brains may be transformed according to individual patients.

Figure 7:
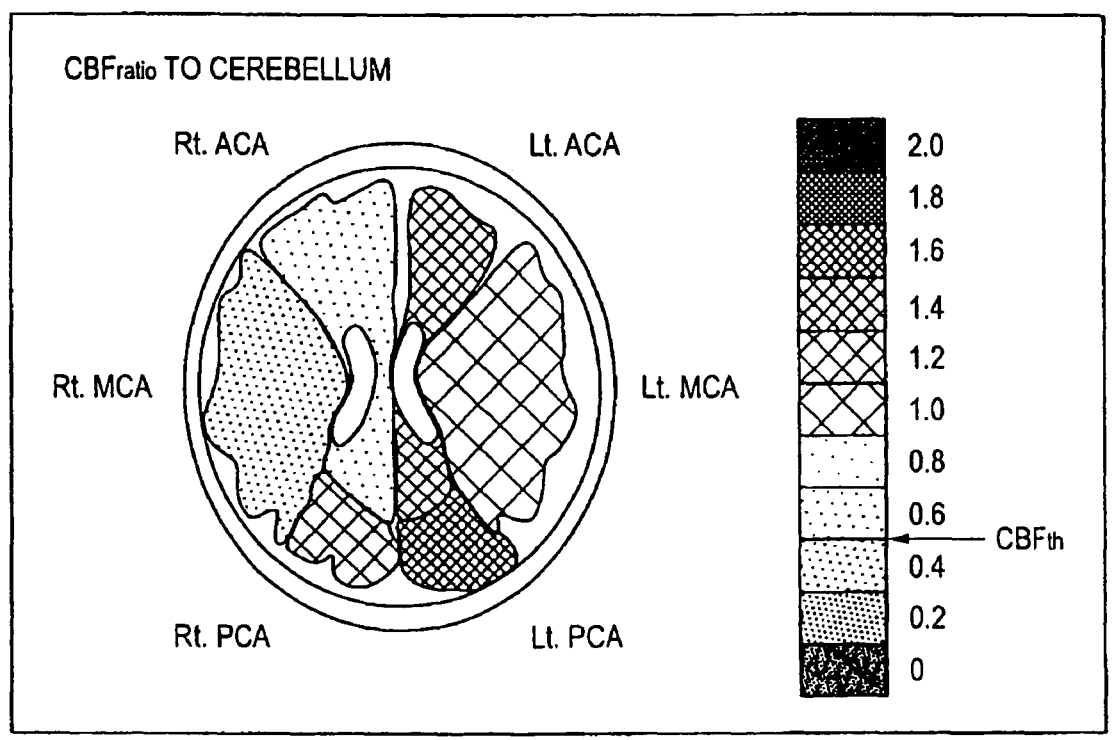
FIG. 7 is a diagram of an example of another display adopted in the embodiment.
Figure 8:
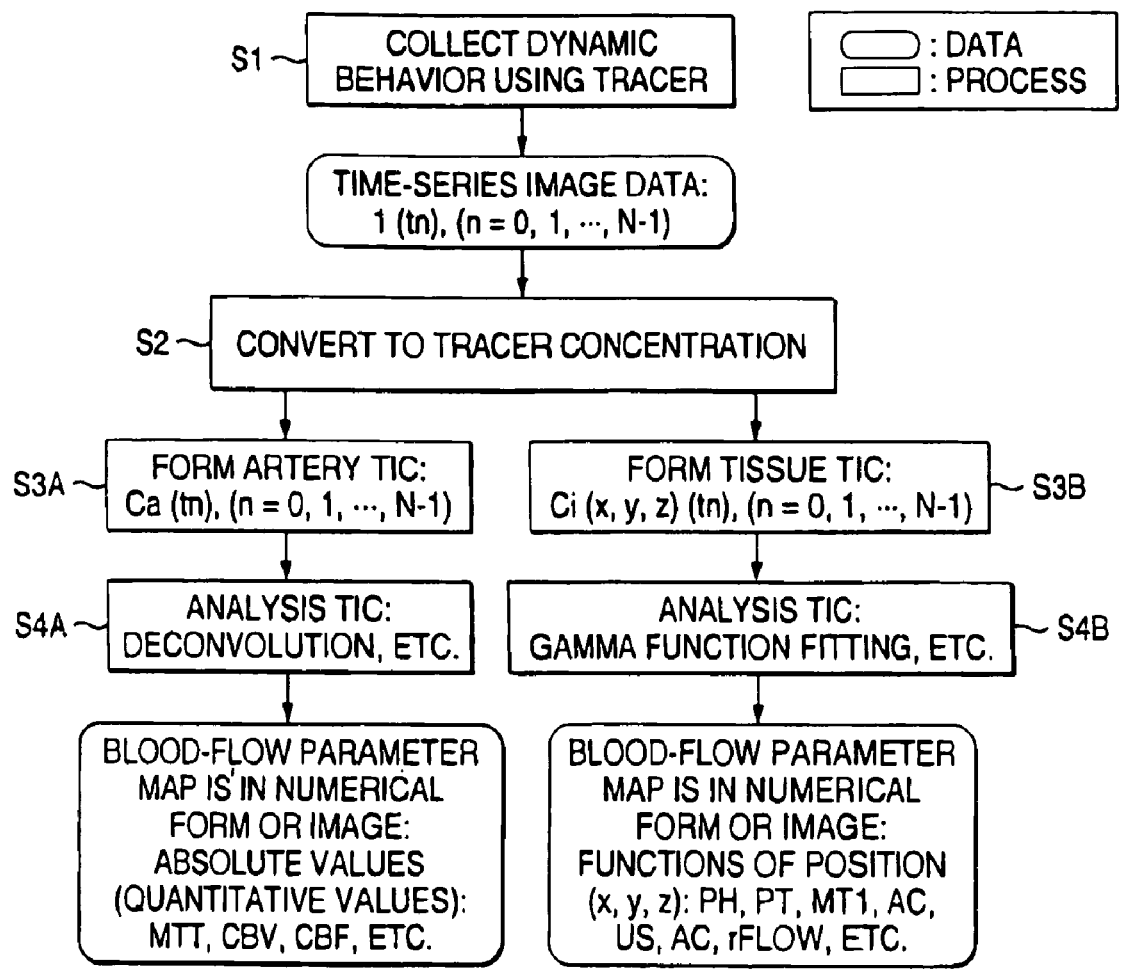
FIG. 8 is a schematic flowchart for a conventional dynamic-study analysis process.
Figure 9:
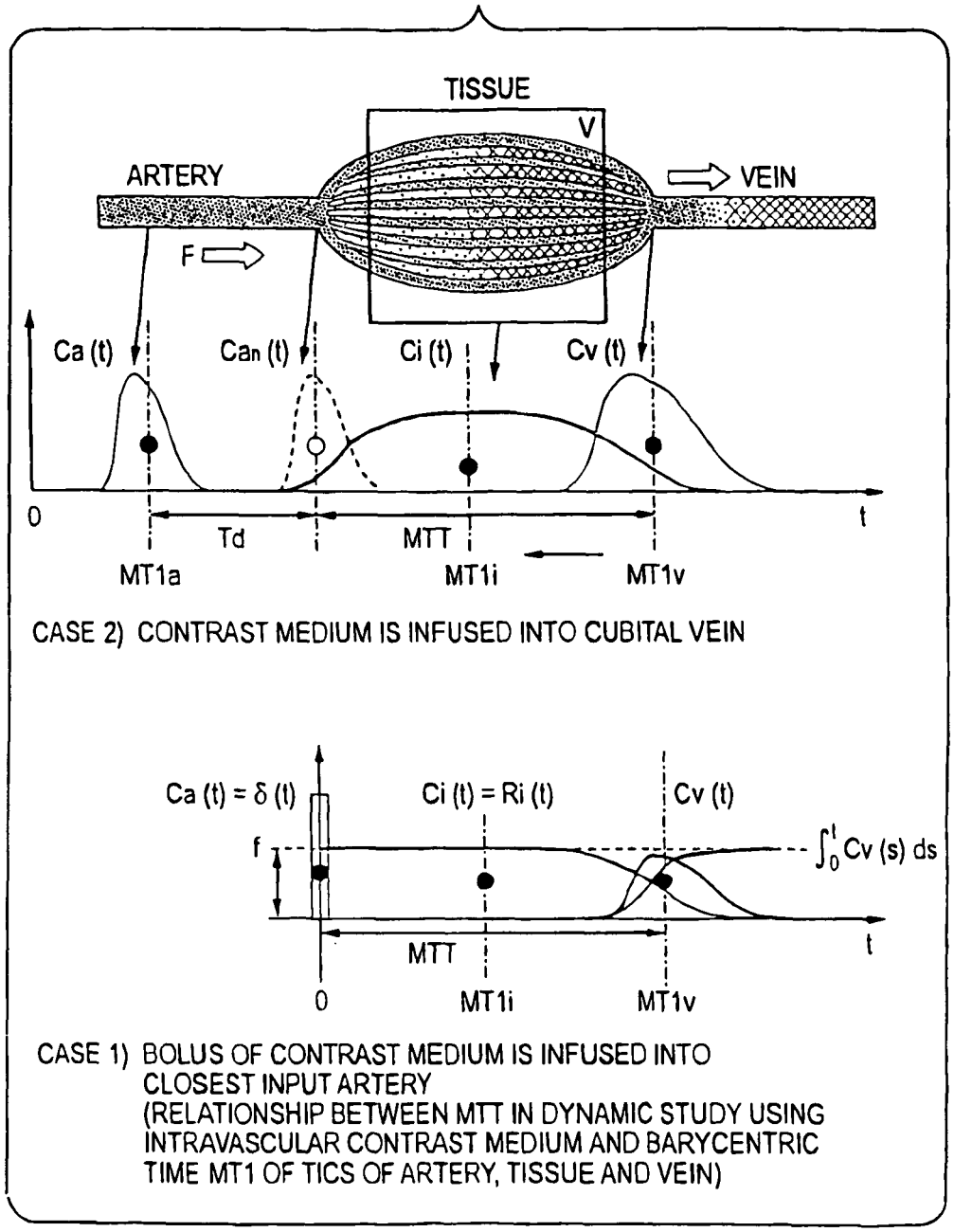
FIG. 9 is a diagram for explaining the relationship between a blood vessel model and the measurement of TIC in dynamic study.
Figure 10:
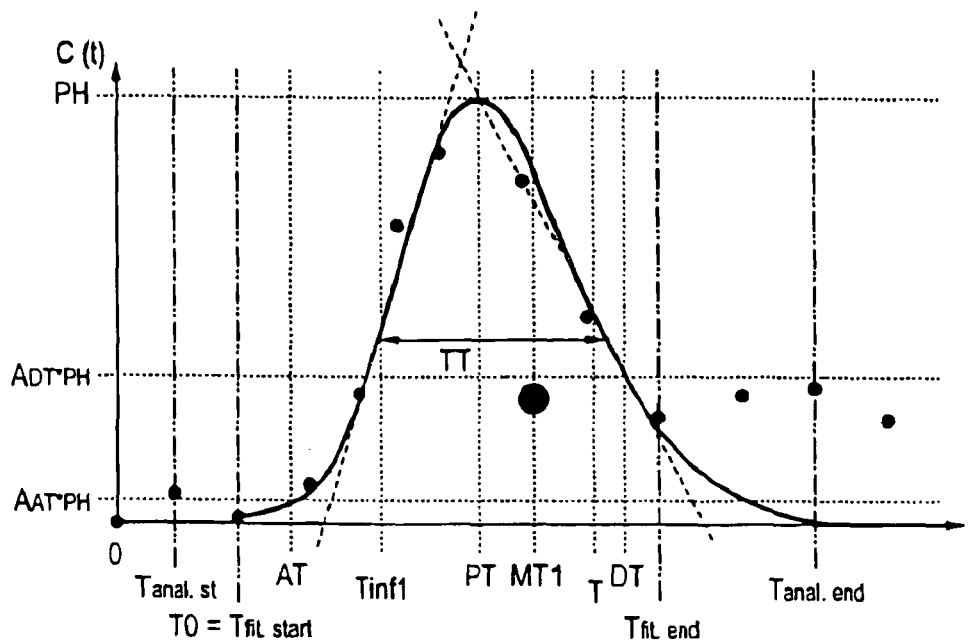
FIG. 10 is a diagram for explaining gamma function fitting in dynamic study.
Figure 11:
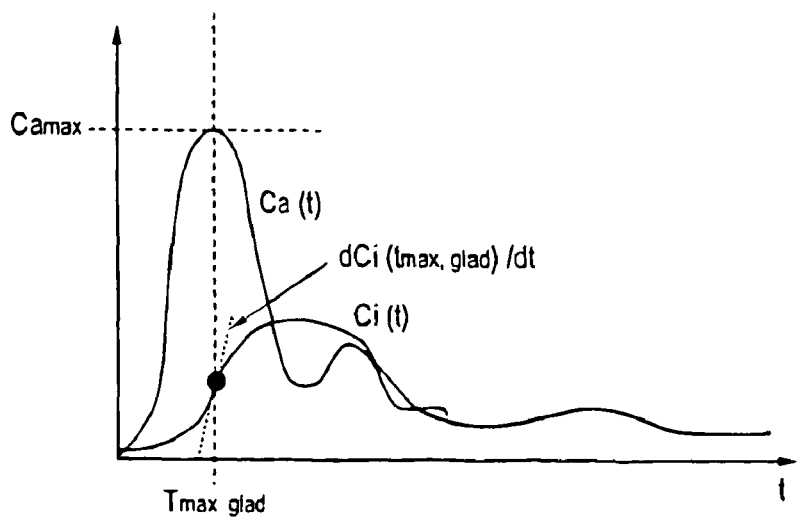
FIG. 11 is a diagram for explaining a maximum gradient method.
Figure 12:
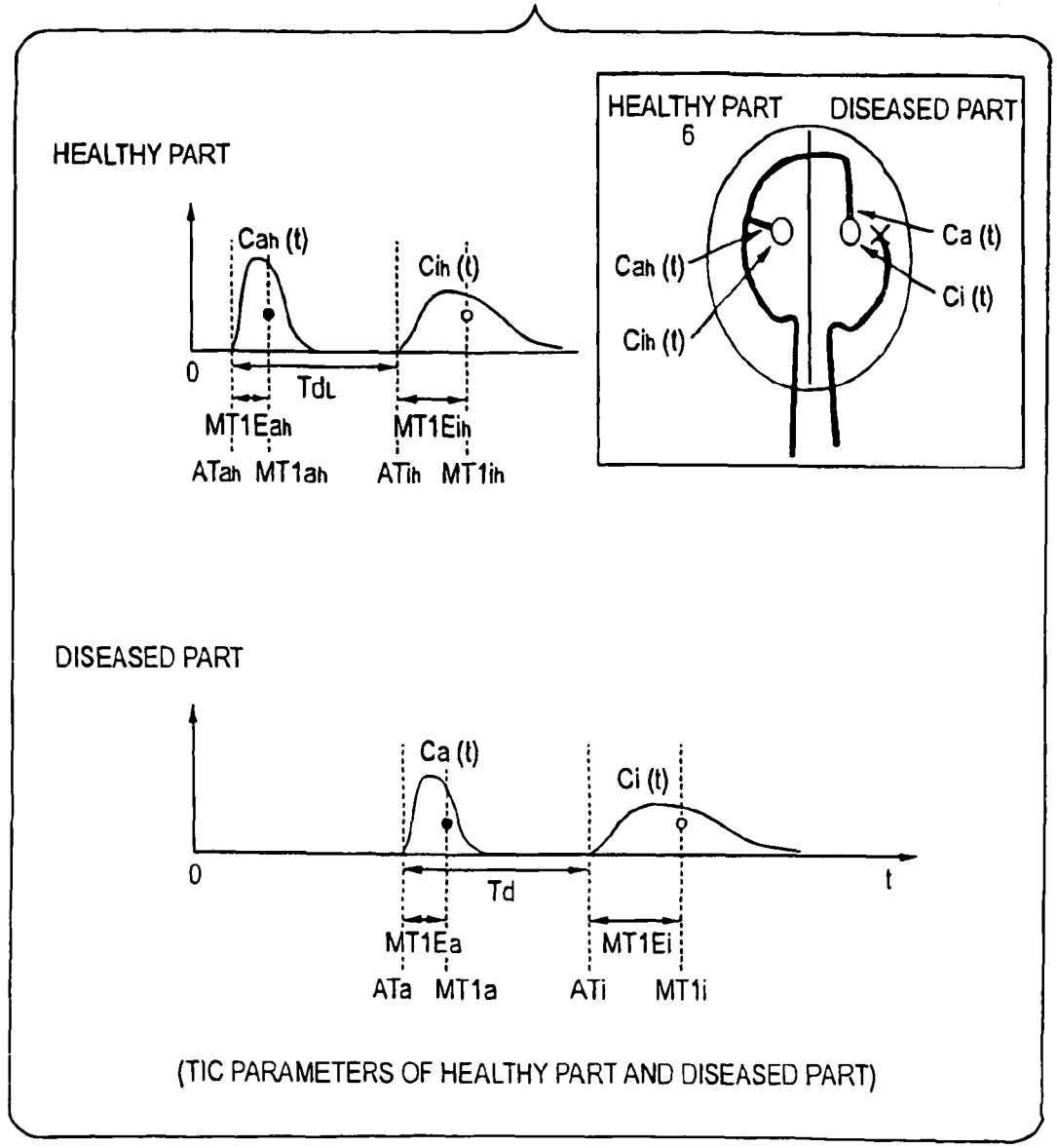
FIG. 12 is a diagram for explaining parameters of TIC and those related to TIC of a healthy part and a diseased part in the conventional blood-flow analysis.

FIG. 7 shows an example of the display of results colored for each control region, in which the ratio to a normal value for each control region is displayed in color, allowing the degree of the risk in each region to be recognized in numerical values and color. The color indicated by 1 in the color bar is expressed as a normal value. For example, as color comes close to red, a blood-flow disease becomes serious. Thresholds which are required for statistics can also be displayed together. The display is not necessarily for each control region but may be for each pixel. It is preferable to redivide the scale division of the color bar stepwise automatically for the statistics of the parameters when possible maximum value and minimum value are given.

In plotting of (c) on a graph, two parameters are plotted on a two-dimensional graph in ordinate and abscissa, in which the data of each control region of a specific individual is indicated by a mean value and a standard deviation SD. The reason for displaying SD is to see the distribution in ROI. Since large SD indicates a large variation in the control region, the reader is recommended to review the plotting, such as to divide the region finer. In this case, an ellipse is shown because of two variables. The two variables are delta-MTT and CBVratio for the centroid method and CBVratio vs. CBFratio for the maximum gradient method. The variables may be absolute values when the absolute values are calculated by the optional function, in which case since three values, CBV, CBF, and MTT can be calculated even by the two methods, two of which can be plotted on a graph or, alternatively, a three-dimensional graph is possible.

Figure 6B:
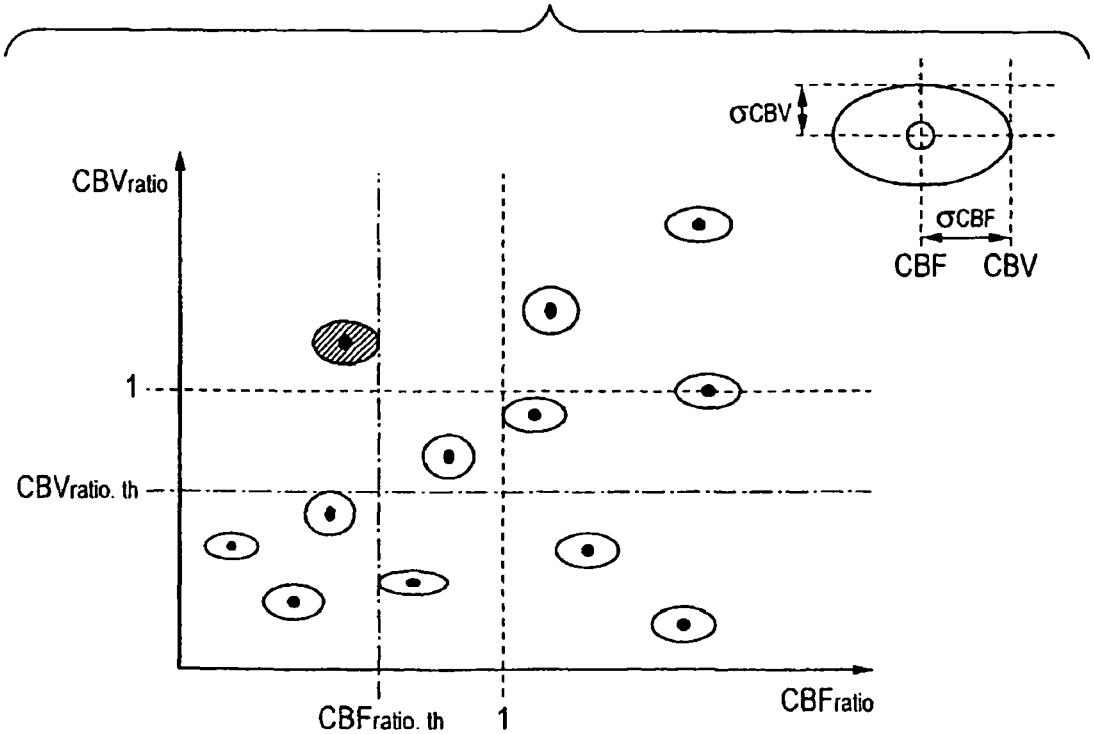
FIG. 6B is a diagram of another example of a display adopted in the embodiment.

FIG. 6B shows a display example of a two-dimensional graph showing the relationship between CBVratio and CBFratio which are the ratios to the reference region of a specified control region (an MCA area in this case). The graph is made for each control region. The points on the graph indicate the respective mean values of CBVratio and CBFratio and the SDs in ROI in an elliptic form. Since the SDs in the ordinate and the abscissa are different, they form an elliptic form. They may not necessarily be in an elliptic form but may be in the shape of cross. Numeral 1 denotes the normal value of each parameter. It is preferable to display a plotted point, e.g., in a specific color or flash to make it easy to view at that time. CBFratio.th and CBVratio.th are threshold values which are considered to be clinically dangerous in statistics, wherein 1 indicates a normal value. The displayed value may be the ratio to the normal value or the difference from the normal value, in which case 0 is the normal value. The database fills up with an increasing number of samples.

Here a supplementary description of the significance of displaying the blood-flow parameters, for example, on the two-dimensional graph will be given.

A living body has the function that when the blood pressure of a downstream artery decreases due to the clogging or stenosis of an upstream artery, the artery expands while having a self regulation capability, thereby maintaining the flow rate. More specifically, for cerebral tissues, when the blood pressure decreases to extend MTT, the living body expands the blood vessels to increase CBV, thereby maintaining CBF. This will be specifically described with reference to the two-dimensional graph of CBVratio vs. CBFratio for example. When the following relations hold, CBVratio>1, MTTratio>1, CBFratio>CBFratio.th this indicates that the brains have regulation capability, thus having a high curative effect. Conversely, if the relation CBFratio>CBFratio.th is satisfied but CBVratio<1 and MTTratio>1 hold, this indicates that the regulation capability decreases, thus having a low curative effect.

Observing the positions of the two parameters on the graph provides information that cannot be given only by CBF. Since there are the problems of the number of data, measuring accuracy, and differences among individuals, the threshold for a living body cannot be determined by a binary logic. Parameters grouped according to the combination of the values thereof and in a clinical viewpoint is displayed on a graph in advance by statistical calculation. They are compared to the plotted patient's values, so that even nonspecialists can visually understand the condition of the patient. Expressing not only the blood-flow parameters but also, for example, diffusion coefficient ADC for MRI and a blood flow rate with MRA in dimensions allows more diversified diagnosis.

(6. Providing Medical Information and Medical Control)

Not only the analyses are displayed in the form of images or graphs but also the amount of drugs used for treatment etc. can be calculated from acquired inspection information (step S46 of FIG. 5) and can be provided to doctors and/or can be inputted directly to the drug infusion unit 31 through the catheter 32 (step S47). Although a treatment necessary group and a treatment unnecessary group overlap with each other, the necessity of treatment can be known by indicating the reliability in color or numerically. When one of treatment and storage must be selected or the statistic distribution (mean values and SDs) of CBF and CBV in each group is known, it may be determined in binary logic by Bayesian decision method. The data can also be reflected not to the binary-logic decision of treatment/no treatment but to the amount of drugs such that the larger the value determined from the two functions CBFratio and CBVratio which are continuous values, the more a thrombolytic drug is applied. The function of dosage can be expressed as:

thrombolytic drug dosage=function (CBVratio, CBFratio, age, sex, heart rate, or blood pressure)

Thus necessary information are presented for organic processing from diagnosis through determination of a therapeutic method by the apparatus. Particularly, blood-flow information is applied to diseases that need an urgent remedy such as cerebral infarction and myocardial infarction, thus offering significantly important function.

(7. Effects)

Blood-flow information is frequently applied to diseases with high urgency such as cerebral infarction and myocardial infarction. According to this embodiment, necessary information can be provided not only for diagnosis but also to treatment. For this purpose, it is important to express blood-flow information on a common scale that does not depend on the individuals and inspection method.

A first point of the embodiment is that new indices are proposed to provide high-quality information which is comparative in a common condition as database and a specific calculation method is presented on the basis of a theoretical endorsement. The conventional method has a small range of application and so has no generality such that comparison across inspection units cannot be performed with simple relative values (the area AC of tissue TIC, barycentric time: MT1, etc. in this case) and the comparison can be used only for a specified patient because it depends on the inspection technique and cardiopulmonary functions.

On the other hand, since the parameters calculated by the method of using the ratios and differences are general values, they can be made a database not only for one inspection method in a single modality but also for the entire MRI and beyond modality.

A second point of the embodiment is that, since there is no need to measure artery TIC as inspection method, it is easier than the conventional absolute-value quantification method, and the problem, which is specific to DSC-MRI, can be solved that the measuring accuracy of artery TIC is low due to the problems of linearity with intensity and the dynamic range and as such, measuring accuracy can be decreased contrarily because of the problem of delay time. Also the parameters can be compared to a database which is stored in the form of a healthy-part ratio or a cerebellum ratio not in the form of absolute values by another modality.

A third point of the embodiment is excellent in that not only the processes from collection through diagnosis to determination of treatment can be completed as one inspection but also data acquired by the conventional method can be reused.

A fourth point of the embodiment is that diagnosis can be performed while comparing the data to the stored database and a final diagnostic guide can be provided.

According to the embodiment, the ratio to a normal value and relation to a threshold are seen directly even if they are not seen only with a map by a nonspecialist. This allows even emergency doctors or duty doctors who are not specialized in cerebral blood flow to make a diagnosis. This is an important function for patients with cerebral infarction who require immediate treatment. Moreover, it is quite obvious that the function contributes to an improvement in treatment of cerebral infarction and myocardial infarction which are now the second and third principal causes of death.

What is claimed is:

1. A blood-flow analysis apparatus for analyzing a time intensity curve (TIC) for each pixel or region of interest of time-series images collected by imaging a desired region of a sample over time with a medical modality by applying a tracer to the blood of the sample, the analysis apparatus comprising:
    a calculation unit configured to calculate and output parameters indicative of blood-flow dynamics peculiar to a measured tissue of the sample as ratio to, or difference from, parameters at a desired reference region on the basis of only the time intensity curve of the measured tissue, said calculated parameters including blood flow based on the ratio of a rising maximum gradient of the time intensity curve of the tissue to the rising maximum gradient of the time intensity curve of the reference region; and
    an output display unit for visually presenting calculated parameters output by the calculation unit.

2. The blood-flow analysis apparatus according to claim 1, wherein:
    the calculation unit is configured to include means for using parameters of a region that is regarded as a healthy part of an image as the reference region, wherein, if the desired region is a bilaterally symmetrical organ, the reference region is a healthy region of the pair and, if the desired region is a brain, the reference region is a substantially stable region irrespective of sample, or a phantom with a known flow rate.

3. The blood-flow analysis apparatus according to claim 2, further comprising:
    at least one of (a) a unit configured to set the reference region manually, and (b) a unit configured to set the reference region automatically.

4. The blood-flow analysis apparatus according to claim 3, wherein:
    an automatic setting unit is configured to set a template formed in a fixed or transformable state on a standardized image.

5. The blood-flow analysis apparatus according to claim 1, wherein:
    the calculation unit is configured to calculate the parameters: blood volume based on the ratio of the area under the time intensity curve of the tissue to the area under the time intensity curve of the reference region; and a mean transit time based on mean transit time=blood volume/blood flow.

6. The blood-flow analysis apparatus according to claim 5, wherein:
    the output display unit displays a mean value or standard deviation of at least one parameter in a specified shape for each of divided control regions of the desired region on a graph of dimensions corresponding to the number of the parameters.

7. The blood-flow analysis apparatus according to claim 6, wherein:
    the graph is a three-dimensional graph; and
    the parameters include blood flow, blood volume, and mean transit time.

8. The blood-flow analysis apparatus according to claim 6, wherein:
    the graph is a two-dimensional graph; and
    the parameters include blood flow and blood volume.

9. The blood-flow analysis apparatus according to claim 6, wherein:
    the graph is a two-dimensional graph; and
    the parameters include blood volume and difference in mean transit time.

10. The blood-flow analysis apparatus according to claim 6, wherein:
    the display unit displays a threshold of clinically necessary treatment and a plurality of regions in which the values of the parameters corresponding to the dimensions are grouped statistically from a clinical viewpoint and plots the parameters on the graph.

11. The blood-flow analysis apparatus according to claim 6, wherein:
    the output display unit displays a map and a color bar at the same time, the map displaying at least one of the parameters in color and in stages for each of the divided control regions or pixel of the desired region and the color bar displaying the stages.

12. The blood-flow analysis apparatus according to claim 6, further comprising:
    at least one of (a) a unit configured to set control regions of the desired region manually, and (b) a unit configured to set the control regions of the desired region automatically.

13. The blood-flow analysis apparatus according to claim 5, wherein:
    the calculation unit comprises an absolute-value calculation unit configured to calculate absolute values of the parameters calculated by the calculation unit for each pixel or region of interest when absolute values are given as quantitative values of the parameters of the reference region.

14. The blood-flow analysis apparatus according to claim 1, wherein:
    the calculation unit is configured to calculate the parameters: a difference in mean transit time based on the difference between a barycenter of the time intensity curve of the tissue and a barycenter of the reference region and a coefficient depending on the model; and a blood volume based on the ratio of the area under the time intensity curve of the tissue to the area under curve of the reference region.

15. The blood-flow analysis apparatus according to claim 1, further comprising:
a therapeutic-information providing output unit configured to provide output from the calculation unit as therapeutic information.

16. The blood-flow analysis apparatus according to claim 15, wherein the therapeutic-information providing output unit comprises:
a unit configured to determine information on the dosage of a thrombolytic drug and the position of an administered blood vessel as the therapeutic information with reference not only to parameters of the blood flow, but also to biological information on the sample.

17. The blood-flow analysis apparatus according to claim 1, wherein:
the blood-flow analysis apparatus is integrated with the medical modality.

18. The blood-flow analysis apparatus according to claim 17, wherein:
the medial modality comprises an X-ray CT scanner or a susceptibility contrast MRI scanner.

19. A blood-flow analysis apparatus for analyzing a time intensity curve for each pixel or region of interest of time-series images collected by imaging a desired region of a sample over time with a medical modality by applying a tracer to the blood of the sample, the analysis apparatus comprising:
calculation means configured to calculate and output parameters indicative of blood-flow dynamics peculiar to measured tissue of the sample as a ratio to, or difference from, the parameters at a desired reference region on the basis of only the time intensity curve of the tissue, said calculated parameters including blood flow based on the ratio of a rising maximum gradient of the time intensity curve of the tissue to the rising maximum gradient of the time intensity curve of the reference region; and
an output display means for visually presenting calculated parameters output by the calculation means.

20. A blood-flow analysis method for analyzing a time intensity curve (TIC) for each pixel or region of interest of time-series images collected by imaging a desired region of a sample over time with a medical modality by applying a tracer to the blood of the sample, the analysis method comprising:
using said medical modality to measure a time intensity curve of the tissue of the sample;
using at least one programmed processor configured to calculate parameters indicative of blood-flow dynamics peculiar to measured tissue as ratio to, or difference from, parameters at a desired reference region on the basis of only the time intensity curves of the measured tissue and reference region, said calculated parameters including blood flow based on the ratio of a rising maximum gradient of the time intensity curve of the tissue to the rising maximum gradient of the time intensity curve of the reference region; and
outputting a visual display presenting said calculated parameters.

* * * * *